United States Patent [19]

Tanikawa

[11] 4,443,077
[45] Apr. 17, 1984

[54] FILM CASSETTE AND A PHOTOGRAPHING DEVICE USING THE SAME

[75] Inventor: Kowji Tanikawa, Tokyo, Japan

[73] Assignee: Olympus Optical Co., Ltd, Tokyo, Japan

[21] Appl. No.: 258,946

[22] Filed: Apr. 30, 1981

[30] Foreign Application Priority Data

May 2, 1980 [JP] Japan .................................. 55-58988

[51] Int. Cl.³ ............................................. G03B 17/26
[52] U.S. Cl. ...................................... 354/21; 354/275
[58] Field of Search ..................... 354/21, 75, 76, 275, 354/217, 218, 289; 242/71.1, 71.2, 197; 352/31-33, 37, 78 C, 5; 360/1, 97, 133; 353/15, 19

[56] References Cited

U.S. PATENT DOCUMENTS

| 3,439,598 | 4/1969  | Weitzner et al. | 352/32    |
| 3,592,535 | 7/1971  | Gerry           | 353/15 X  |
| 3,593,635 | 11/1971 | Seruetnick      | 354/275 X |
| 4,141,629 | 2/1979  | Mattes          | 352/5     |
| 4,173,401 | 11/1979 | Harvey          | 354/21    |

FOREIGN PATENT DOCUMENTS 50-113225  9/1975  Japan .
51-8928   1/1976  Japan .

Primary Examiner—William B. Perkey
Attorney, Agent, or Firm—Frishauf, Holtz, Goodman and Woodward

[57] ABSTRACT

A film cassette provided with a magnetic disc for recording data relative to a film. The magnetic disc of the film cassette makes two revolutions when one frame of the film is wound up. Data stored in the magnetic disc are read out during the first revolution of the disc, and renewed data are recorded on the disc during the second revolution.

4 Claims, 5 Drawing Figures

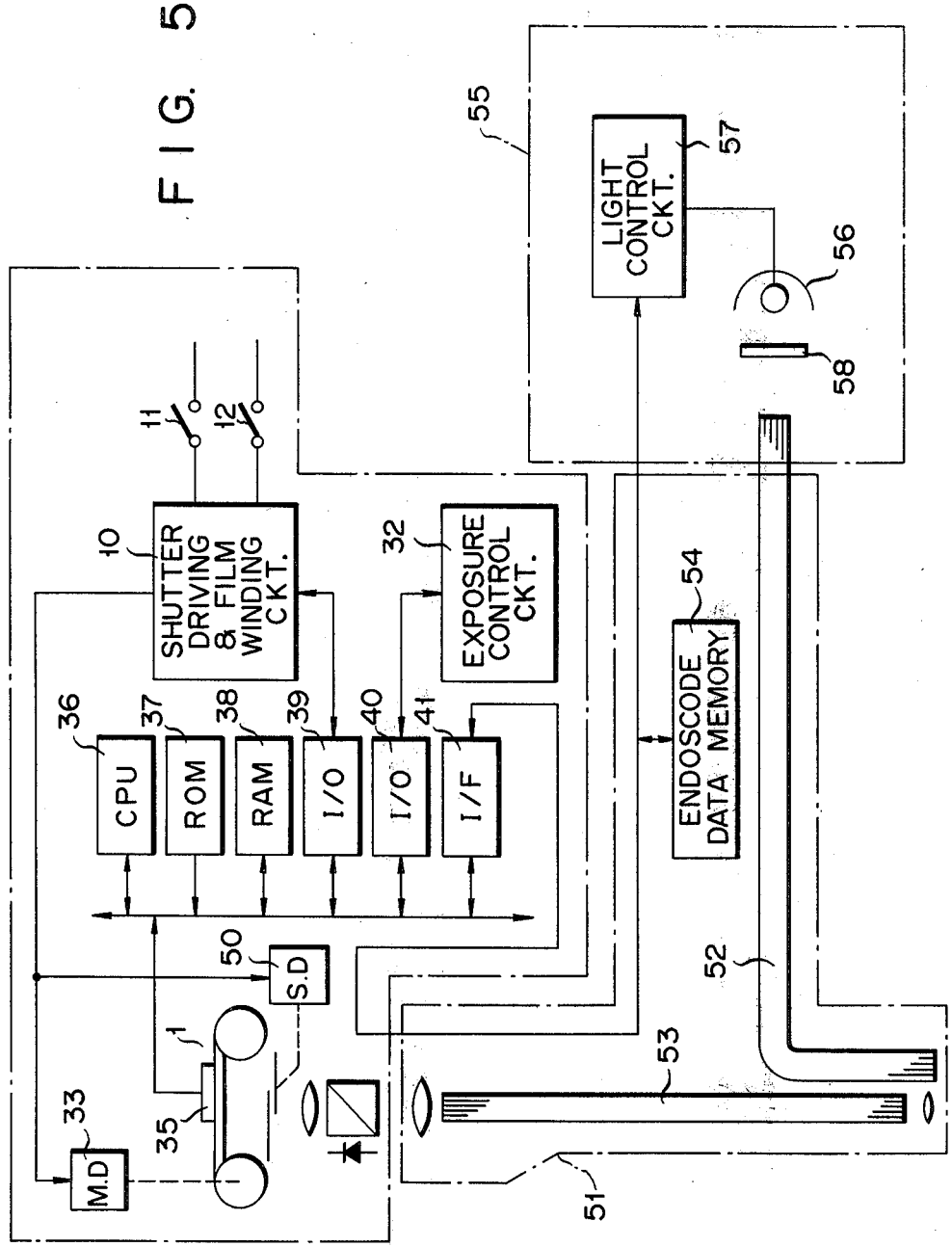

FILM CASSETTE AND A PHOTOGRAPHING DEVICE USING THE SAME

BACKGROUND OF THE INVENTION

This invention relates to a film cassette and a film-cassette type photographing device.

In general, the state of film consumption in a film cassette is perceived by observing a film counter provided in a camera. Film counters include one which counts the number of used or exposed frames of a film and one which indicates the number of unexposed or remaining frames. The counter indicating the number of unexposed frames is so constructed that, after manually setting the number of usable frames in advance, 1 is subtracted from the set frame number with every shot. One such film counter is reset when the back cover of the camera is opened. Accordingly, when a partially used film is set in the camera after it is once taken out from the camera for some purpose, the number of used or unused frames of the film cannot be recognized because the film counter is reset. This leads to inconvenience in photography.

Accordingly, an object of this invention is to provide a film cassette having a recording medium capable of recording film data including at least the number of frames of a film.

Another object of the invention is to provide a film-cassette type photographing device which is loaded with a film cassette having a data recording medium and can perform recording and reproduction of data on and from the recording medium of the film cassette, as well as a photographing operation.

SUMMARY OF THE INVENTION

According to the invention, the recording medium is attached to the outside of the film cassette, and film data including at least the number of frames of a film are recorded on the recording medium. The recording and reproduction of the data on and from the recording medium are performed when the film cassette is set in the camera and with every shot.

BRIEF DESCRIPTION OF THE DRAWINGS

FIG. 5 is a schematic diagram showing a film cassette and a film-cassette type photographing device using the same according to still another embodiment of the invention.

DETAILED DESCRIPTION

Figure 1:
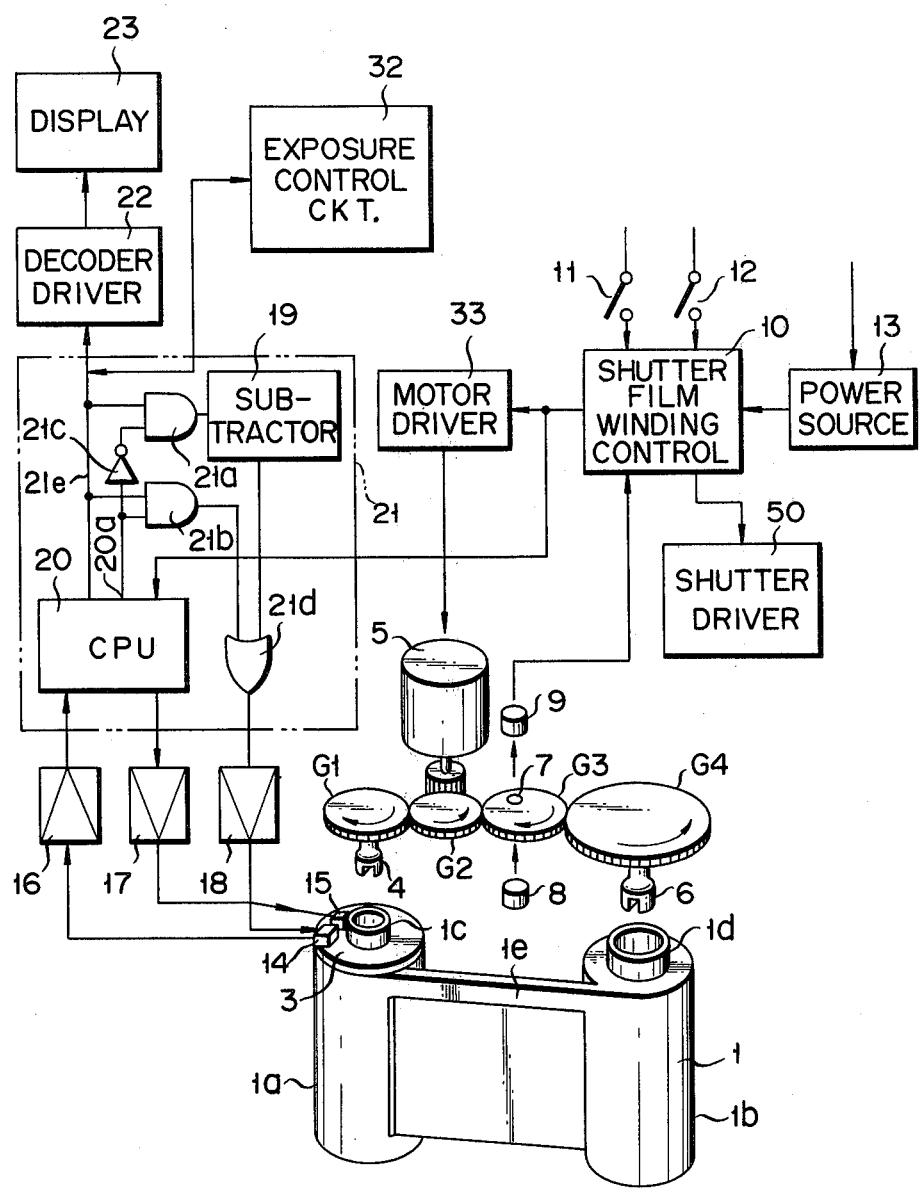
FIG. 1 is a schematic diagram showing a film cassette and a camera loaded therewith according to an embodiment of this invention.
Figure 2:
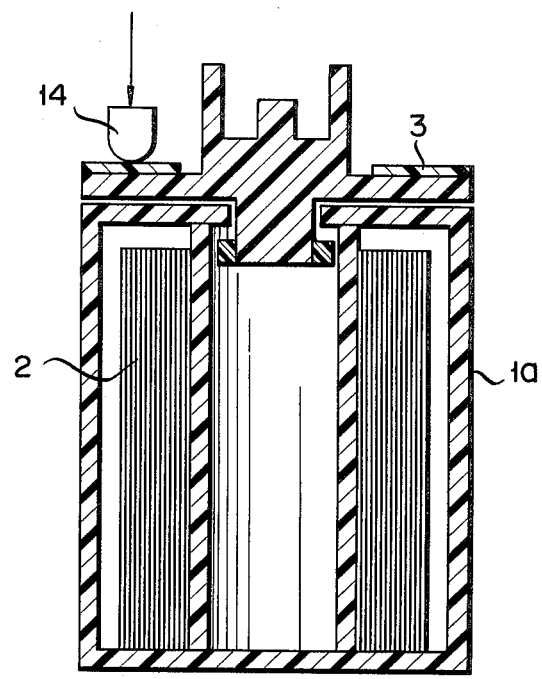
FIG. 2 is a sectional view of the film cassette of FIG. 1.

As shown in FIGS. 1 and 2, a film cassette 1 includes an unexposed film chamber section 1a, a film take-up chamber section 1b, and a bridge section 1e connecting these two chamber sections 1a and 1b. Contained in the unexposed film chamber section 1a is an unexposed film 2. The frames of the film 2 are to be successively wound up and transferred to the film take-up chamber section 1b by means of a film take-up spool 1d after photographing or exposure. A magnetic recording disc 3, which is rotatably mounted on the upper end portion 1c of the unexposed film chamber section 1a, is removably coupled with a shaft 4 of a driving gear G1. The gear G1 is in mesh with a driving gear G2 which is in mesh with the gear of a motor 5. Further, the driving gear G2 is coupled with a film winding gear G4 by means of a gear G3. A shaft 6 of the film winding gear G4 is removably coupled with a spool 1d of the film take-up chamber section 1b. The gear G3 has a bore 7 through which a light emitting element 8 and a light receiving element 9 face each other. The light receiving element 9 is connected to a shutter driving and film winding control circuit 10. The control circuit 10, which may be a conventional motor driver circuit, is connected to a release switch 11, a cassette cover switch 12, and a driving power source 13 of a camera.

Against the recording surface of the magnetic recording disc 3 abut a read-write magnetic head or recording-reproducing head 14 and an erasing head 15. The recording-reproducing head 14 is connected with a control circuit such as a CPU 20 and the output end of an OR gate 21d of a recording control section 21 via amplifiers 16 and 18, respectively. The erasing head 15 is connected with the output end of an amplifier 17. The input end of the amplifier 17 is connected with the CPU 20. The readout data output end of the CPU 20 is connected to a display 23 through a data line 21e and a decoder-driver latch circuit 22. CPU 20 is also connected to an exposure control circuit 32 through data line 21e. Moreover, the data output end of CPU 20 is connected to respective inputs of AND gates 21a and 21b. The gate control signal output 20a of the CPU 20 is connected to the other input of the AND gate 21a through an inverter 21c, and also to the other input of the AND gate 21b. The output of the AND gate 21a is connected to a subtractor 19. The respective outputs of the subtractor 19 and the AND gate 21b are connected to the amplifier 18 through an OR gate 21d. The output of the shutter driving and film winding control circuit 10 is connected to the CPU 20, a motor driver circuit 33, and a shutter mechanism section 50.

Figure 3:
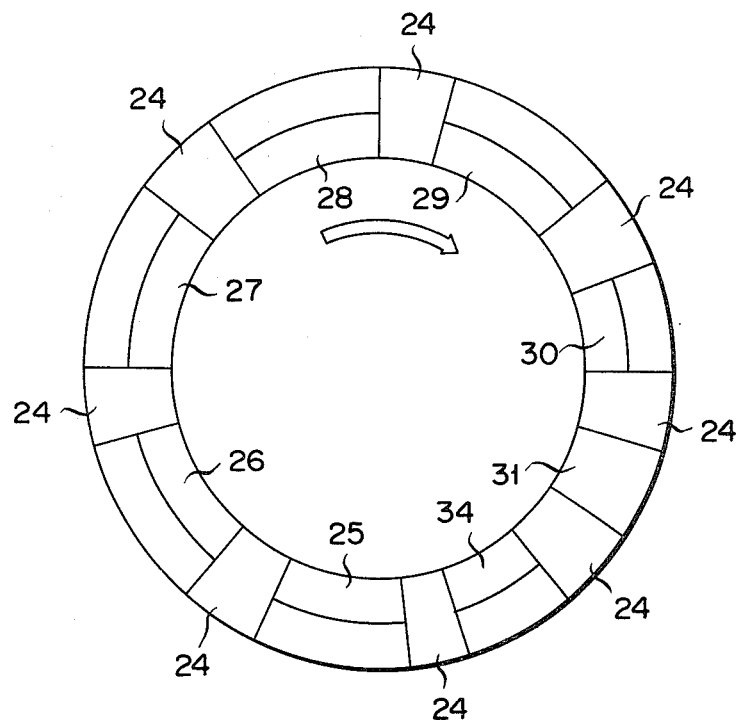
FIG. 3 shows a data format of a recording disc of the film cassette of FIG. 1.

There will now be described the operation of the above-mentioned film cassette and the camera using the same. As shown in FIG. 3, the recording surface of the magnetic recording disc 3 carries a plurality of recording fields divided by blank regions 24, including a frame number data field 25, ASA information field 26, film type data field 27, overdevelopment data field 28, film available period data field 29, filter data field 30, exposure correction data field 31, and flag data field 34. When the camera is loaded with the film cassette 1 having the recording disc 3 on which data are severally recorded in these fields, the cassette cover switch 12 is closed. At this time, if the driving power source 13 is on, the control circuit 10 supplies a start signal to the motor driving circuit 33 and to the CPU 20 of the recording control circuit 21. Then, the motor 5 rotates to wind up the leader of the film contained in the film cassette 1. At the same time, the recording disc 3 is rotated by the shaft 4 which rotates in mesh with the gear G1. The disc 3 makes two revolutions as the film is wound by rotating the spool 1d through an angle of 104°. During the first revolution of the disc 3, the data stored in the disc 3 are reproduced or read out by the recording-reproducing head 14. The frame number data represent the number of practically usable frames exclusive of the leader and trailer of the film. If such number is 20, for example, then frame number data representing 20 frames is read out when the initial leader of the film is wound up, and is supplied to the CPU 20 via the reproducing amplifier 16. Monitoring flag data, the CPU 20 produces a "1" level signal from its gate control signal output 20a when it recognizes that the wound frame of the film is the leader. As a result, the read frame number data is recorded in the original recording area by the recording-reproducing head 14 through the AND gate 21b and the OR gate 21d. When the disc 3 makes its second revolution, the recording-reproducing head 14 reproduces the same data again. The frame number data reproduced for the second time is supplied to the display 23 through the amplifier 16, CPU 20, and decoder-driver latch circuit 22, and is indicated on the display 23. The number of revolutions of the disc 3 is detected in accordance with output pulses from the light receiving element 9, and winding of one frame is recognized at the second revolution of the disc 3.

Subsequently, when the release switch 11 is closed, the shutter driving and film winding control circuit 10 actuates the shutter mechanism section 50. When the operation of the shutter mechanism section 50 is completed, the shutter driving and film winding control circuit 10 drives the motor 5 through the motor driving circuit 33 to wind up the film. As the film is wound up, the recording disc 3 rotates so that the data recorded on the disc 3 are read out. At this time, the CPU 20 recognizes one shot by a signal from the control circuit 10, and delivers a "0" level signal from its gate control signal output 20a. Accordingly, the read frame number data is supplied to the subtracter 19 via the AND gate 21a. The subtractor 19 produces frame number data representing a frame number "19" obtained by subtracting 1 from the aforesaid frame number "20". This output frame number data is supplied to the recording-reproducing head 14 via the OR gate 21d and the amplifier 18, and is recorded on the recording disc 3. The frame number data renewed by the second revolution of the disc 3 is read out and indicated on the display 23. Thereafter, the same operation is repeated until the frame number (remaining frame number) data becomes 0. When the remaining frame number data becomes 0, the trailer of the film is wound up automatically, and thus exposure of all the frames of the film is completed. At this time, overdevelopment data, filter data, and exposure correction data are recorded in their corresponding fields of the recording disc 3. These data are used so that an automatic developer may develop the film under optimum conditions. In the flag data field 34, "0" is recorded when the film is not used, and "1" is recorded when the film is used, that is, when the leader of the film is wound up.

Now there will be described a case where the film cassette 1 is set again in the camera after it is once taken out of the camera when the number of remaining or unexposed frames is 10. In this case, the first one of the 10 unexposed frames is automatically wound up as a leader. Therefore, it is necessary to take away 1 for the wound frame from the number of unexposed frames. Such deduction is performed when the CPU 20 detects that the flag data is "1" which indicates the use of the film. Namely, when the flag data is "1", the CPU 20 produces a gate control signal of terminal 20a to open the AND gate 21a even in the same state as the state of leader winding. Accordingly, the remaining frame number data is supplied through the AND gate 21a to the subtractor 19, where 1 is subtracted from the number of unexposed frames, 10. Thereafter, the aforementioned operation is repeated.

As described above, the state of the film in the film cassette, such as the number of unexposed frames, may be easily detected by renewing with every shot various photographing data recorded on a recording medium which is attached to the film cassette.

Figure 4:
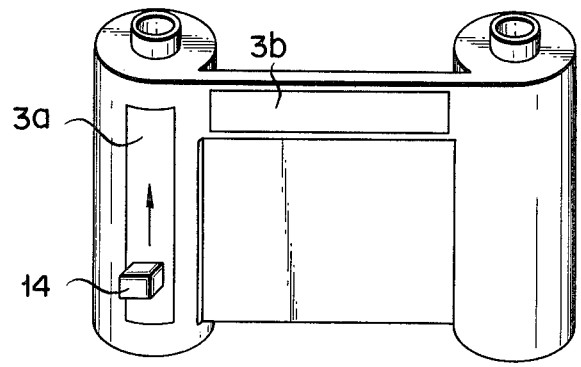
FIG. 4 is a perspective view of a film cassette according to another embodiment of the invention.

In the above-mentioned embodiment, a magnetic recording disc is used for the magnetic recording medium, and reproducing, erasing and recording operations are performed by rotating the disc. Alternatively, however, a fixed recording disc may be used with a recording-reproducing head and an erasing head which are rotated for reproducing, erasing and recording operations. Further, the reproducing, erasing and recording operations may be performed by means of a single head, with increased number of revolutions of the recording disc. The recording disc may be rotated by using an exclusive-use motor instead of utilizing the film winding motor. The recording medium is not limited to the magnetic disc. As shown in FIG. 4, for example, a magnetic strip may be attached to the surface of the film cassette, such as the side end face of the unexposed film chamber section, the flank of the cassette, or the bridge section, so that the head may be reciprocated on the magnetic strip for recording and reproducing operations. Alternatively, moreover, a magnetic material may be applied to the film cassette.

Referring now to FIG. 5, there will be described another embodiment of this invention. In this embodiment, the film cassette 1 is provided with a RAM 35, and the invention is applied to an endoscopic photographing device. An endoscopic camera 50 is provided with a CPU 36 for controlling the photographing device, a ROM 37 storing a necessary program for the control, a RAM 38 for reading and writing data, I/O controllers 39 and 40, and an interface 41. An endoscope 51 is provided with a memory 54 storing data on the endoscope 51, such as data corresponding to the calibers of a light guide fiber 52 and an image guide fiber 53. A light supply device 55 is provided with a light source 56 which is on-off controlled by a light control circuit 57. The light control circuit 57 includes a memory for storing filter data indicating the existence and type of a filter 58. According to this embodiment, a series of photographing operations are performed in accordance with the program stored in the ROM 37. In this case, the data in the date fields 25 to 30 and 34 shown in FIG. 3 are all stored in the RAM 35 of the film cassette 1. The RAM 35 is formed of a memory backed up by a battery or a nonvolatile memory.

According to this invention, as described above, a film cassette is provided with a recording medium capable of recording and reproducing by electrical or magnetic means. Since the number of unexposed frames and other data can be recorded on the recording medium, a camera using the film cassette requires neither a film counter nor a reset mechanism therefor, so that the mechanical part of the camera may be simplified in construction. Moreover, the number of remaining unexposed frames of even a partially used film can be understood correctly, and entirely used films may be discriminated with ease.

Furthermore, development may be performed with high efficiency since development information including the photographing conditions (type of light source, exposure correction, etc.) and the propriety of overdevelopment can be recorded electrically or magnetically.

Since many data items are stored in the film cassette, the camera can be automatically set so that right exposure may be effected by utilizing such data.

What is claimed is:

1. A film cassette comprising:
   an unexposed film chamber section containing unexposed frames of a film;
   a film take-up chamber section having a film take-up spool for winding up the film in said unexposed film chamber section;
   a bridge section connecting said unexposed film chamber section and said film take-up chamber section; and
   a recording medium attached to at least one of said unexposed film chamber section, said film take-up chamber section and said bridge section, and on and from which film data relative to each one-frame of photographing are recorded and reproduced thereby to update the film data for each recording;
   said recording medium comprising a magnetic disc rotatably mounted on said unexposed film chamber section and rotating in concert with a film winding action.

2. A film cassette according to claim 1, wherein said film data relative to each one frame of photographing comprises frame number data.

3. A film cassette comprising:
   an unexposed film chamber section containing unexposed frames of a film;
   a film take-up chamber section having a film take-up spool for winding up the film in said unexposed film chamber section;
   a bridge section connecting said unexposed film chamber section and said film take-up chamber section; and
   a recording medium attached to at least one of said unexposed film chamber section, said film take-up chamber section and said bridge section, and storing data relative to the film;
   said recording medium comprising a magnetic disc rotatably mounted on said unexposed film chamber section and rotating in concert with a film winding action.

4. A film cassette according to claim 3, wherein said stored data relative to the film comprises frame number data.

* * * * *